(12) United States Patent
Miyazaki et al.

(10) Patent No.: US 7,015,020 B2
(45) Date of Patent: Mar. 21, 2006

(54) PREPARATION OF 2-KETO CARBOXYLIC ACID FROM CARBON DIOXIDE

(75) Inventors: Masaya Miyazaki, Tosu (JP); Hideaki Maeda, Tosu (JP); Hiroyuki Nakamura, Tosu (JP); Noriyuki Yamada, Tosu (JP); Masao Shibata, Tosu (JP)

(73) Assignee: National Institute of Advanced Industrial Science and Tecnology, Tokyo (JP)

( * ) Notice: Subject to any disclaimer, the term of this patent is extended or adjusted under 35 U.S.C. 154(b) by 133 days.

(21) Appl. No.: 10/344,236

(22) PCT Filed: Mar. 13, 2002

(86) PCT No.: PCT/JP02/02362

§ 371 (c)(1),
(2), (4) Date: Feb. 11, 2003

(87) PCT Pub. No.: WO02/095046

PCT Pub. Date: Nov. 28, 2002

(65) Prior Publication Data

US 2004/0009565 A1 Jan. 15, 2004

(30) Foreign Application Priority Data

May 22, 2001 (JP) .............................. 2001-153178

(51) Int. Cl.
*C12P 7/62* (2006.01)

(52) U.S. Cl. ...................... 435/135; 435/136; 435/189; 435/191; 435/232

(58) Field of Classification Search ................ 435/135, 435/136, 232, 189, 191
See application file for complete search history.

(56) References Cited

U.S. PATENT DOCUMENTS 5,631,143 A * 5/1997 Menart et al. ............. 435/69.1

OTHER PUBLICATIONS

Foppen, et al., Recl. Trav. Chim. Pays-Bas, vol. 109, No. 5, pp. 359-360 (1991).
Miyazaki, et al., Chemical Communiations, vol. 18, pp. 1800-1801, (Aug. 2001) Cambridge, United Kingdom.
Wiesser, et al., Journal of Molecular Catalysis B Enzymatic, vol. 11, No. 4-6, pp. 179-184, (2001).

* cited by examiner

*Primary Examiner*—Leon B. Lankford, Jr.
(74) *Attorney, Agent, or Firm*—Wenderoth, Lind & Ponack, L.L.P.

(57) ABSTRACT

The invention discloses a novel method for the preparation of a 2-keto carboxylic acid from carbon dioxide by an enzymatic addition reaction with an aldehyde compound. Carbon dioxide, which can be in the form of carbonate ions, is reacted with an aldehyde compound such as acetaldehyde and propionaldehyde under mild reaction conditions in the presence of a decarboxylase to give a 2-keto carboxylic acid such as pyruvic and a 2-ketobutyric acid by a reverse reaction to the enzymatic decarboxylation reaction. The scope of the invention involves contribution to a solution of the environmental problem of global warming due to carbon dioxide as a greenhouse effect gas in the aerospace.

4 Claims, 1 Drawing Sheet

PREPARATION OF 2-KETO CARBOXYLIC ACID FROM CARBON DIOXIDE

TECHNICAL FIELD

The present invention relates to a method for the preparation of a 2-keto carboxylic acid, which can readily be converted into a corresponding carboxylic acid, from carbon dioxide or, more particularly, to a method for the preparation of a 2-keto carboxylic acid by utilizing carbon dioxide, which is a potential environmental pollutant, as an effective chemical resource.

BACKGROUND ART

As a countermeasure to the serious environmental problem of global warming, it is required in recent years to substantially decreasing the greenhouse effect by various so-called greenhouse gases of which carbon dioxide is one of the most notorious pollutant gases. Reducing of carbon dioxide in the aerospace can be accomplished by decreasing emission of the gas but can also be accomplished by increasing fixation or immobilization of the carbon dioxide gas from emission sources.

A great variety of proposals are made heretofore for the ways of fixation of carbon dioxide in an emission source including absorption in the oceanic water, electrochemical reactions for the synthesis of hydrocarbon compounds such as methane or alcoholic compounds such as methanol from carbon dioxide, quasi-photosynthesis reaction for the synthesis of methanol and so on. Though limited to a laboratory scale experimentation, a method has been developed for the fixation of carbon dioxide gas to produce a carboxylic acid by a quasi-enzymatic reaction in the presence of a metal complex catalyst or in an organic synth sis reaction.

It is a general tr nd in recent years in this regard that certain enzymatic reactions have made their second debut by virtue of their advantages of the relatively small load imposed on the environment. This advantage of low load on the environment, however, can hardly be obtained in the fixation of carbon dioxide according to the above mentioned various methods because of the considerably large energy consumption in the methods and indispensability of using an organic solvent in the reactions.

A report is also available of utilization of an enzymatic reaction for fixation of carbon dioxide. The enzymatic reaction so far developed, however, is limited to the enhancement of water-solubility of carbon dioxide by means of a carbonate dehydratase.

DISCLOSURE OF INVENTION

Figure 1:
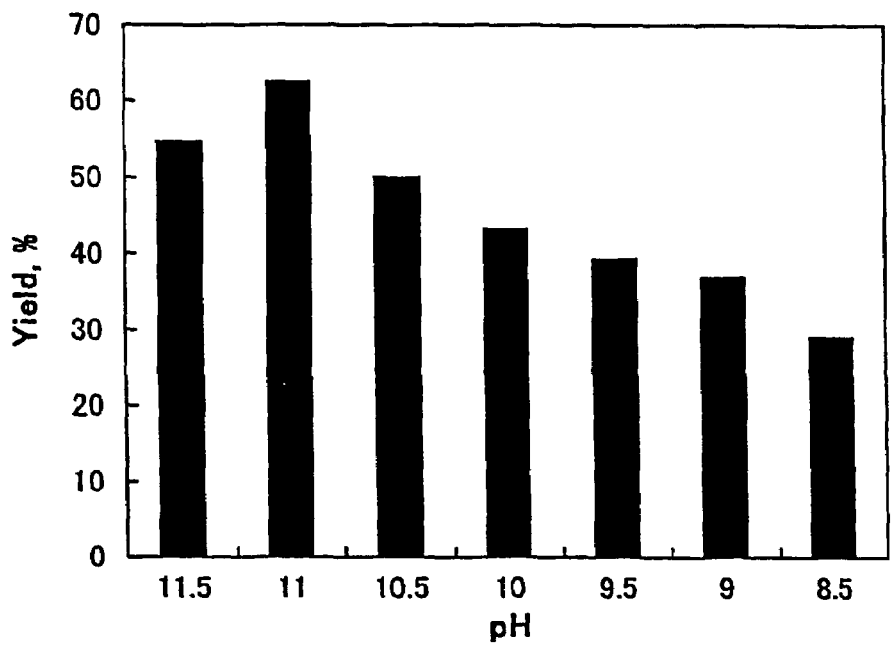
FIG. 1 is a bar chart showing the pH-dependency of the yield of pyruvic acid produced in Example 1.

The present invention accordingly has an object to provide a means for the synthetic preparation of a low molecular-weight 2-keto carboxylic acid compound from carbon dioxide as a chemical resource to serve as a starting material by utilizing a specific enzymatic reaction which is not liable for a heavy load imposed on the environment.

Thus, the method provided by the present invention for the synthetic preparation of a 2-keto carboxylic acid from carbon dioxide as a starting reactant comprises the step of reacting carbon dioxide with an aldehyde compound in the presence of a decarboxylase to effect an addition reaction which is a reverse reaction to the enzymatic decarboxylation reaction f a 2-ket carboxylic acid.

The form of the carbon dioxid used to pertain to th above-described inventive method is not particularly limitative and can be any of gaseous carbon dioxide, liquefied carbon dioxide, supercritical carbon dioxide and carbonate ions.

As is mentioned above, the enzymatic addition reaction proceeding in the inventive method between carbon dioxide and an aldehyde compound is a reverse reaction to the decarboxylation reaction proceeding in the presence of a decarboxylase. The carbon dioxide to pertain to the inventive method can be, besides the gaseous, liquid and supercritical forms, in the form of carbonate ions as is the case in an aqueous solution of a water-soluble carbonate compound as in a sodium carbonate-based buffer solution.

The 2-keto carboxylic acid compound as the reaction product of the inventive method naturally differs depending on the aldehyde compound to be reacted with carbon dioxide. Among various known decarboxylases, pyruvic acid decarboxylase is preferred in respect of the relatively good versatility for various aldehyde compounds. When carbonate ions are reacted with acetaldehyde, for example, by utilizing a pyruvic acid decarboxylase in the presence of thiamin, the reaction product is pyruvic acid. When liquid carbon dioxide is reacted at 25° C. with acetaldehyde in a mixed solution of the thiamin/pyruvic acid decarboxylase and acetaldehyde, pyruvic acid can be obtained. The efficiency for the production of pyruvic acid by the same reaction as above can be improved when the reaction is conducted in supercritical carbon dioxide.

A variety of 2-keto carboxylic acids other than pyruvic acid can be prepared by using different combinations of the aldehyde compounds and the decarboxylase. A preferable reaction medium in which the reaction of the invention is conducted is an alkaline buffer solution having a pH value in the range from 10 to 12 or, more preferably, in the vicinity of pH 11. The reaction temperature in this case is preferably in the range from 10 to 40° C. or, more preferably, at or in the vicinity of 25° C.

The reaction mixture after completion of the reaction in the above-described manner can be subjected to an isolation and purification treatment of the 2-keto carboxylic acid as the target product by a conventional procedure of reversed-phase chromatography. When the inventive method is conducted by adequately selecting the reaction conditions, the 2-keto carboxylic acid as the purified target product can be obtained in a yield of 50% or higher relative to the amount of the aldehyde compound used as the starting reactant.

In the following, the method of the present invention is described in more detail by way of Examples which, however, never limit the scope of the invention in any way.

EXAMPLE 1

A 1 ml portion of a 0.1M sodium carbonate buffer solution having a varied pH value was admixed with acetaldehyde in a concentration of 0.1 mM, thiamin in a concentration of 1 $\mu$M and 1 unit of a commercially available pyruvic acid decarboxylase and the mixture was agitated for 1 hour at 25° C. to effect the enzymatic addition reaction of the acetaldehyde with the carbonate ions. The above-mentioned 1 unit of the enzyme is an amount of the enzyme capable of decarboxylating 1.0 μmole of pyruvic acid to form acetaldehyde. After completion of the reaction, the reaction mixture was admixed with 100 μl of a 1M hydrochloric acid and then subjected to a high-performance liquid chromatographic analysis by using a silica gel column of 4.0 mm diameter and 150 mm length (Wakosil C-18AR, a product by Wako Jun-yaku Co.) at 25° C. with a 0.05% aqueous TFA (trifluoroacetic acid) solution as the eluant at a flow rate of 1 ml/minute.

The yields of the pyruvic acid product for the respective pH values were calculated by using a calibration curve pr pared in advance with known sampl s f pyruvic acid. The r sults are shown by the bar chart graph of FIG. 1 from which it is understood that the yield of the pyruvic acid depended on the pH value giving the highest yield of 62% when the pH was 11.

EXAMPLE 2

Figure 2:
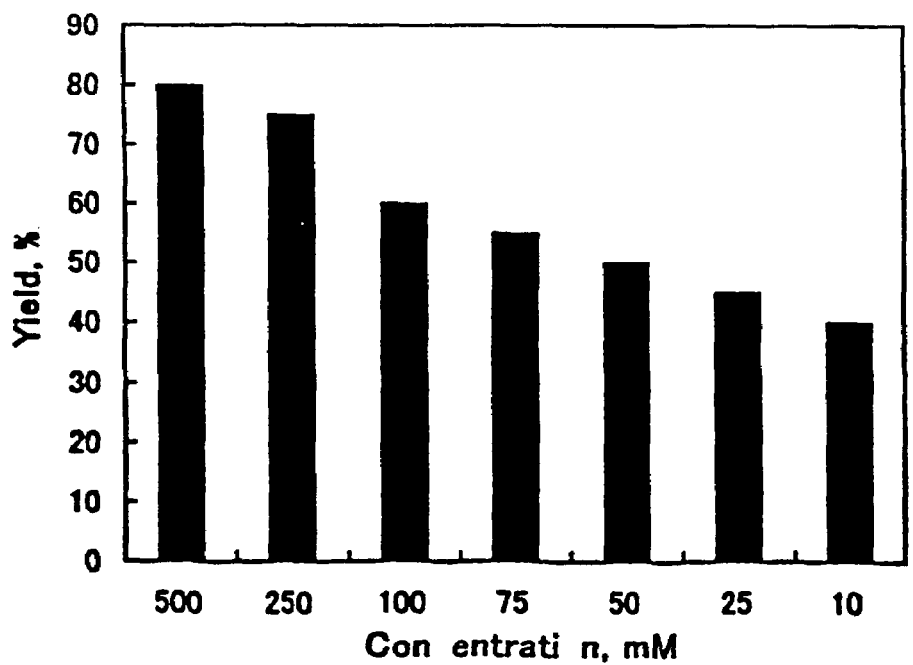
FIG. 2 is a bar chart showing the dependency of the yield of the pyruvic acid product on the concentration of the sodium carbonate buffer solutions prepared in Example 2.

The same enzymatic addition reaction as in Example 1 was conducted at 25° C. for 1 hour by using sodium carbonate buffer solutions in varied concentrations each having a pH of 11 in place of the buffer solutions having varied pH values. Each of the reaction mixtures after completion of the reaction was subjected to the high-performance liquid chromatographic analysis in the same manner as in Example 1 to calculate the yield of the pyruvic acid product for the respective concentrations. The results were as shown in FIG. 2 by the bar chart from which it is understood that the yield of the product was increased as the concentration of the buffer solution was increased giving the highest value of 82% with a concentration of 0.5 M within the range tested.

EXAMPLE 3

A 2 ml portion of a 0.5M tris/hydrochloric acid buffer solution having a pH of 8.8 was admixed with acetaldehyde in a concentration of 0.1 mM, thiamin in a concentration of 1 μM and 1 unit of the pyruvic acid decarboxylase and then admixed with 3 ml of liquefied carbon dioxide. The reaction mixture was agitated for 1 hour at 25° C. under pressurization to effect the reaction. The reaction mixture after completion of the reaction was subjected to the chromatographic analysis in the same manner as in Example 1 to give a result that the yield of the pyruvic acid product was 50%.

EXAMPLE 4

The same enzymatic addition reaction as in Example 1 was repeated excepting for the replacement of the acetaldehyde with the same molar amount of propionaldehyde to give a result that the product was 2-ketobutyric acid in a yield of 52% when the sodium carbonate buffer solution had a pH of 11.

What is claimed is:

1. A method for the preparation of a 2-keto carboxylic acid from carbon dioxide in the form of carbonate ions which comprises: reacting said carbon dioxide in the form of carbonate ions with an aldehyde compound in the presence of a pyruvic acid decarboxylase in an aqueous medium having a pH value in the range from 10 to 12.

2. The method for the preparation of a 2-keto carboxylic acid according to claim 1 wherein the reaction of said carbon dioxide in the form of carbonate ions and an aldehyde compound is conducted at a temperature in the range from 10 to 40° C.

3. The method for the preparation of a 2-keto carboxylic acid according to claim 2 wherein the reaction is conducted in a carbonate buffer solution.

4. The method for the preparation of a 2-keto carboxylic acid according to claim 3 wherein the carbonate buffer solution contains thiamine.

* * * * *

UNITED STATES PATENT AND TRADEMARK OFFICE
CERTIFICATE OF CORRECTION

| | |
|---|---|
| PATENT NO. | : 7,015,020 B2 |
| APPLICATION NO. | : 10/344236 |
| DATED | : March 21, 2006 |
| INVENTOR(S) | : Masaya Miyazaki et al. |

It is certified that error appears in the above-identified patent and that said Letters Patent is hereby corrected as shown below:

Title page, item (73), please change

"National Institute of Advanced Industrial Science and Tecnology" to --National Institute of Advanced Industrial Science and Technology--.

Signed and Sealed this

Second Day of October, 2007

JON W. DUDAS
*Director of the United States Patent and Trademark Office*